US00PP12196P2

(12) United States Plant Patent
Bellion

(10) Patent No.: US PP12,196 P2
(45) Date of Patent: Nov. 6, 2001

(54) HIBISCUS PLANT NAMED 'FLORU'

(75) Inventor: Gabrielle Bellion, Le Thoureil (FR)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 09/639,893

(22) Filed: Aug. 16, 2000

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—A Para
(74) *Attorney, Agent, or Firm*—C. A. Whealy

(57) ABSTRACT

A distinct cultivar of Hibiscus plant named 'Floru', characterized by its upright plant habit; dense and bushy plant habit; strong vigorous growth habit; and large and numerous purple-colored flowers.

1 Drawing Sheet

BACKGROUND OF THE INVENTION

The present Invention relates to a new and distinct cultivar of Hibiscus plant, botanically known as *Hibiscus syriacus*, and hereinafter referred to by the cultivar name Floru.

The new Hibiscus is a product of a breeding program conducted by the Inventor in Beaufort-en-Valle, France. The objective of the breeding program was to create new Hibiscus cultivars with good vigor and unique flower colors.

The new Hibiscus originated from a cross by the Inventor of the *Hibiscus syriacus* cultivar Red Heart, not patented, as the male, or pollen, parent with the *Hibiscus syriacus* cultivar Oiseau Bleu, not patented, as the female, or seed, parent. The cultivar Floru was discovered and selected by the Inventor as a flowering plant within the progeny of the stated cross in a controlled environment in Beaufort-en-Valle, France, on the basis of its good vigor and unique flower color.

Asexual reproducton of the new cultivar by cuttings taken at Beaufort-en-Valle, France, has shown the the unique features of this new Hibiscus are stable and reproduced true to type in successive generations.

SUMMARY OF THE INVENTION

Plants of the cultivar Floru have not been observed under all possible environmental conditions. The phenotype may vary somewhat with variegations in environment such as temperature, light intensity, daylength, irrigation amount and frequency, and fertilizer type and rate without, however, any variance in genotype.

The following traits have been repeatedly observed and are determined to be the unique characteristics of 'Floru'. These characteristics in combination distinguish 'Floru' as a new and distinct cultivar.

1. Upright plant habit.

2. When pinched, very freely branching; dense and bushy plant habit.

3. Strong vigorous growth habit.

4. Large and numerous purple-colored flowers.

Plants of the new Hibiscus differ from plants of the male parent, the cultivar Red Heart, primarily in flower color as plants of the cultivar Red Heart have white-colored flowers with a red eye. In addition, plants of the new Hibiscus are more vigorous and stronger than plants of the cultivar Red Heart.

Plants of the new Hibiscus differ from plants of the female parent, the cultivar Oiseau Bleu, in flower color as plants of the cultivar Oiseau Bleu have blue-colored flowers. In addition, plants of the new Hibiscus are more vigorous, faster growing, more freely branching, and more freely flowering than plants of the cultivar Oiseau Bleu.

Plants of the new Hibiscus can be compared to plants of the *Hibiscus syriacus* cultivar Minerva, not patented. In side-by-side comparisons conducted in Grand Haven, Mich., plants of the new Hibiscus differ from plants of the cultivar Minerva in the following characteristics:

1. Plants of the new Hibiscus are faster growing and more freely branching than plants of the cultivar Minerva.

2. Plants of the new Hibiscus have stronger, thicker and less brittle stems than plants of the cultivar Minerva.

3. Plants of the new Hibiscus are more freely flowering than plants of the cultivar Minerva.

4. Flower color of plants of the new Hibiscus is deeper and more saturated than flower color of plants of the cultivar Minerva.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which more accurately describe the actual colors of the new Hibiscus. The photograph comprises a close-up view of a typical flower of 'Floru'.

DETAILED BOTANICAL DESCRIPTION

In the following description, color references are made to The Royal Horticultural Society Colour Chart except where general terms of ordinary dictionary significance are used. Plants were grown in Grand Haven, Mich. under field conditions which closely approximate commercial production conditions. Plants were about 6 month old.

Botanical classification: *Hibiscus syriacus* cultivar Floru.

Parentage:

*Male, or pollen, parent.*—*Hibiscus syriacus* cultivar Red Heart, not patented.

*Female, or seed, parent.*—*Hibiscus syriacus* cultivar Oiseau Bleu, not patented.

Propagation:

*Type cutting.*—By softwood cuttings.

*Time to initiate roots.*—Summer: About 21 days at 32° C. Winter: About 28 days at 20° C.

*Time to produce a rooted cutting or liner.*—Summer: About 56 days at 32° C. Winter: About 70 days at 20° C.

*Root description.*—Thick and fleshy.

Plant description:

*Crop time.*—From rooted liners, about one growing season is required to produce a flowering finished plant in a one-gallon container.

*Form.*—Mostly upright; inverted triangle; dense and bushy perennial.

*Usage.*—Appropriate for one to three-gallon containers.

*Plant height, soil level to top of plant plane.*—About 2.7 m.

*Plant width.*—About 1.75 m.

*Vigor.*—Moderate vigor; rapid growth rate.

*Branching habit.*—When pinched, very freely branching with about 20 lateral branches per plant.

*Lateral branches.*—Length: About 86 cm. Diameter: About 7.5 mm. Internode length: About 4.5 cm. Texture: Smooth. Color: 177A.

*Foliage description.*—Leaves simple, alternate, generally symmetrical and long persisting. Tolerant to stresses. Quantity per lateral branch: Typically about 61. Length: About 6.5 cm. Width: About 4.75 cm. Shape: Rhomboid to ovate, tri-lobed. Apex: Acute. Base: Broadly cuneate to rounded. Margin: Crenate. Texture: Glabrous; thick. Color: Young foliage, upper surface: 146A. Young foliage, lower surface: 146B. Mature foliage, upper surface: 146A; midvein, 146B. Mature foliage, lower surface: 146B; midvein, 146C. Petiole: Length: About 2.5 cm. Diameter: About 2 mm. Color: 146B.

Flower description:

*Flower type and habit.*—Single rounded flowers arising from leaf axils. Freely flowering. Flowers last about one day on the plant. Not persistent. Not fragrant.

*Natural flowering season.*—Continuously flowering from mid-summer through fall.

*Quantity of flowers.*—About 55 per lateral branch; about 1,100 per plant.

*Flower diameter.*—About 13.5 cm.

*Flower depth* (*height*).—About 2.5 cm.

*Flower buds* (*just showing color*).—Length: About 4.5 cm. Diameter: About 1.75 cm. Shape: Elliptical. Rate of opening: About one day. Color: 77A.

*Petals.*—Arrangement/appearance: Single whorl of five petals. Length: About 6.5 cm. Width: About 5.75 cm. Shape: Obovate. Apex: Rounded to obtuse. Margin: Entire; slightly undulate. Texture: Veins, prominent; smooth. Color: Upper surface, when opening: 78B; base and veins, 60A. Lower surface, when opening: 78C. Upper surface, opened flower: 78A; base and veins, 60A; color fading to 78B with development. Lower surface, opened flower: 78B.

*Calyx.*—Shape: Star; sepals, five. Length: About 1.75 cm. Diameter: About 1.75 cm. Sepal shape: Acute; apex, acute; margin, entire. Texture: Smooth; thick. Color: Upper surface: 145A. Lower surface: 144A.

*Peduncle.*—Strength: Moderately strong. Angle: About 25° to the stem. Length: About 1.5 cm. Color: 138A.

*Reproductive organs.*—Stamens: Quantity of anthers per flower: About 45 to 50. Anther length: About 1 mm. Anther color: 11B. Pollen amount: Moderate. Pollen color: 11B. Pistils: Pistil quantity per flower: One. Pistil length: About 3 cm. Stigma shape: Five-parted; rounded. Stigma color: White, close to 155D. Style length: About 3 cm. Style color: White, close to 155D. Ovary color: 193B.

*Seed.*—Length: About 5 mm. Diameter: About 4 mm. Color, immature: 193B.

Disease resistance: Under commercial production conditions, plants of the new Hibiscus have not been observed to be resistant to pathogens common to Hibiscus.

Pest resistance: Under commercial production conditions, plants of the new Hibiscus have been noted to be resistant to slugs.

It is claimed:

1. A new and distinct cultivar of Hibiscus plant named 'Floru', as illustrated and described.

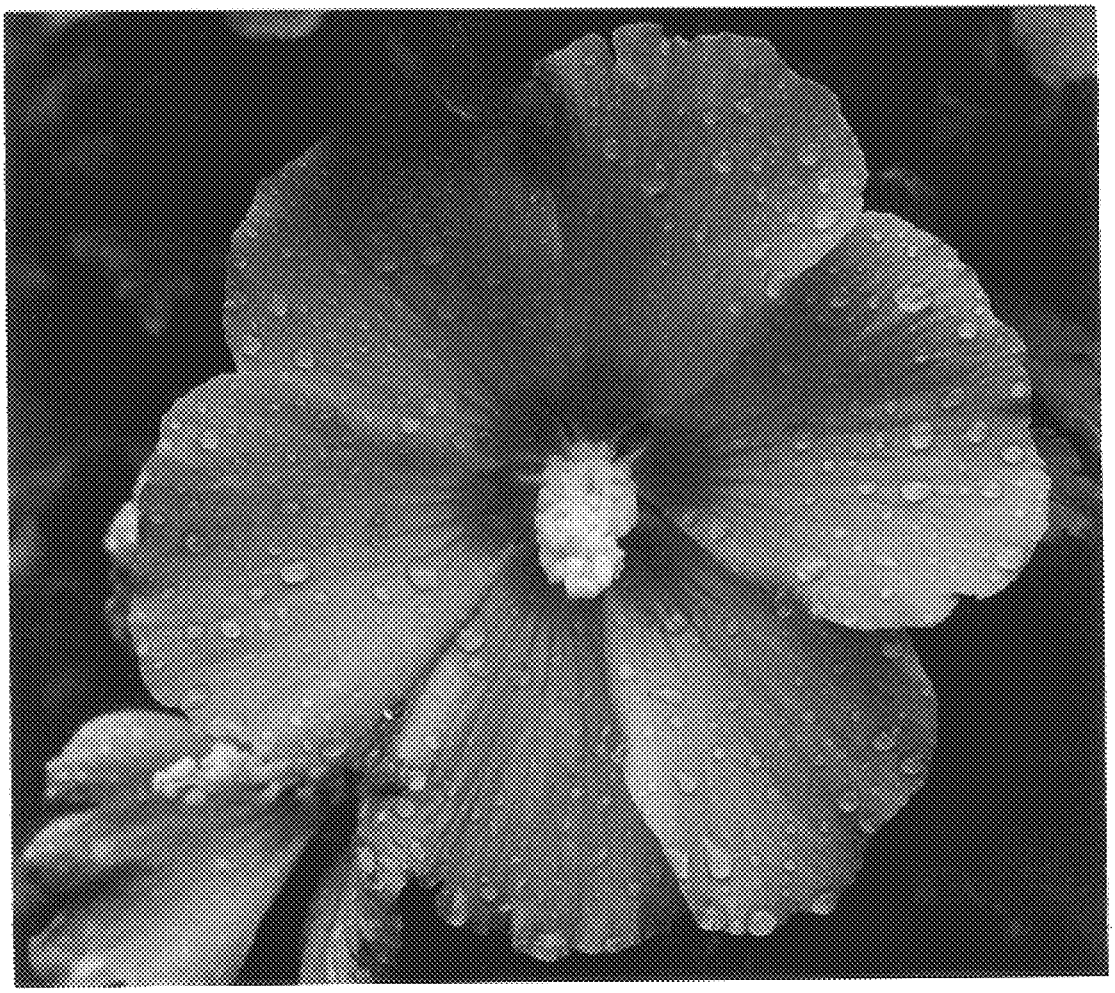

* * * * *